United States Patent
Shemesh et al.

(10) Patent No.: US 10,881,376 B2
(45) Date of Patent: Jan. 5, 2021

(54) SYSTEM AND METHOD FOR PROVIDING AUDITORY GUIDANCE IN MEDICAL SYSTEMS

(71) Applicant: Biosense Webster (Israel) Ltd., Yokneam (IL)

(72) Inventors: Toam Shemesh, Hertziliya (IL); Moshe Ingel, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 472 days.

(21) Appl. No.: 15/807,124

(22) Filed: Nov. 8, 2017

(65) Prior Publication Data

US 2019/0133552 A1 May 9, 2019

(51) Int. Cl.
*A61B 8/00* (2006.01)
*A61B 18/14* (2006.01)
(Continued)

(52) U.S. Cl.
CPC .............. *A61B 8/4272* (2013.01); *A61B 5/04* (2013.01); *A61B 5/0402* (2013.01); *A61B 5/044* (2013.01); *A61B 5/0422* (2013.01); *A61B 5/053* (2013.01); *A61B 5/0538* (2013.01); *A61B 5/061* (2013.01); *A61B 5/6852* (2013.01); *A61B 5/7271* (2013.01); *A61B 5/7415* (2013.01); *A61B 8/085* (2013.01); *A61B 18/1442* (2013.01); *A61B 18/1492* (2013.01); *A61B 5/062* (2013.01); *A61B 5/743* (2013.01); *A61B 5/7425* (2013.01);
(Continued)

(58) Field of Classification Search
CPC ............ A61B 18/1442; A61B 18/1492; A61B 2017/00022; A61B 2017/00106; A61B 2017/00243; A61B 2018/00351; A61B 2018/00577; A61B 2018/00696; A61B 2018/00791; A61B 2018/00839; A61B 2018/00875; A61B 2034/2051; A61B 2560/0468; A61B 2562/04; A61B 2562/06; A61B 5/04; A61B 5/0402; A61B 5/0422; A61B 5/044; A61B 5/053; A61B 5/0538; A61B 5/061; A61B 5/062; A61B 5/6852; A61B 5/7271; A61B 5/7415; A61B 5/7425; A61B 5/743; A61B 5/7435; A61B 8/085; A61B 8/4272
See application file for complete search history.

(56) References Cited

U.S. PATENT DOCUMENTS

| 5,391,199 A | 2/1995 | Ben-Haim |
| 5,443,489 A | 8/1995 | Ben-Haim |
| | (Continued) | |

*Primary Examiner* — Lee S Cohen
*Assistant Examiner* — Tigist S Demie (57) ABSTRACT

An auditory guidance system and method for medical systems and procedures are disclosed. A method for providing auditory guidance during a medical procedure includes selecting a song for playing during the medical procedure. At least a portion of the song is assigned to the medical procedure. Parameter information for at least one parameter associated with the medical procedure is obtained during the medical procedure. The obtained parameter information is compared against predetermined thresholds for each parameter. The portion of the song associated with the parameter information is modified in accordance with the comparison and the modified portion of the song is played to provide auditory guidance during the medical procedure.

8 Claims, 7 Drawing Sheets

(51) Int. Cl.
*A61B 8/08* (2006.01)
*A61B 5/042* (2006.01)
*A61B 5/06* (2006.01)
*A61B 5/053* (2006.01)
*A61B 5/00* (2006.01)
*A61B 5/044* (2006.01)
*A61B 5/04* (2006.01)
*A61B 5/0402* (2006.01)
*A61B 18/00* (2006.01)
*A61B 34/20* (2016.01)
*A61B 17/00* (2006.01)

(52) U.S. Cl.
CPC ... *A61B 5/7435* (2013.01); *A61B 2017/00022* (2013.01); *A61B 2017/00106* (2013.01); *A61B 2017/00243* (2013.01); *A61B 2018/00351* (2013.01); *A61B 2018/00577* (2013.01); *A61B 2018/00696* (2013.01); *A61B 2018/00791* (2013.01); *A61B 2018/00839* (2013.01); *A61B 2018/00875* (2013.01); *A61B 2034/2051* (2016.02); *A61B 2560/0468* (2013.01); *A61B 2562/04* (2013.01); *A61B 2562/06* (2013.01)

(56) References Cited

U.S. PATENT DOCUMENTS

| | | |
|---|---|---|
| 5,558,091 A | 9/1996 | Acker et al. |
| 5,944,022 A | 8/1999 | Nardella et al. |
| 5,983,126 A | 11/1999 | Wittkampf |
| 6,172,499 B1 | 1/2001 | Ashe |
| 6,177,792 B1 | 1/2001 | Govari et al. |
| 6,266,551 B1 | 7/2001 | Osadchy et al. |
| 6,456,864 B1 | 9/2002 | Swanson et al. |
| 6,690,963 B2 | 2/2004 | Ben-Haim et al. |
| 6,788,967 B2 | 9/2004 | Ben-Haim et al. |
| 2003/0074228 A1* | 4/2003 | Walsh ............... A61N 5/1048 705/3 |
| 2006/0106375 A1 | 5/2006 | Werneth et al. |
| 2006/0229594 A1* | 10/2006 | Francischelli ......... A61N 7/02 606/27 |
| 2007/0049827 A1 | 3/2007 | Donaldson |
| 2007/0106289 A1* | 5/2007 | O'Sullivan ......... A61B 18/1492 606/41 |
| 2007/0167943 A1 | 7/2007 | Janssen et al. |
| 2009/0093806 A1 | 4/2009 | Govari et al. |
| 2009/0138007 A1 | 5/2009 | Govari et al. |

* cited by examiner

SYSTEM AND METHOD FOR PROVIDING AUDITORY GUIDANCE IN MEDICAL SYSTEMS

SUMMARY

An auditory guidance system and method for medical systems and procedures are disclosed. A method for providing auditory guidance during a medical procedure includes selecting a song for playing during the medical procedure. At least a portion of the song is assigned to the medical procedure. Parameter information for at least one parameter associated with the medical procedure is obtained during the medical procedure. The obtained parameter information is compared against predetermined thresholds for each parameter. The portion of the song associated with the parameter information is modified in accordance with the comparison and the modified portion of the song is played to provide auditory guidance during the medical procedure.

BRIEF DESCRIPTION OF THE DRAWINGS

A more detailed understanding may be had from the following description, given by way of example in conjunction with the accompanying drawings wherein.

DETAILED DESCRIPTION

Documents incorporated by reference in the present patent application may include terms that are defined in a manner that conflict with the definitions made explicitly or implicitly in the present specification. In the event of any conflicts, the definitions in the present specification should be considered to be controlling.

Cardiac ablation is a medical procedure performed by electrophysiologists that may be used to correct heart rhythm defects, known as arrhythmias, by creating lesions to destroy tissue in the heart that contributes to the rhythm defects. An example arrhythmia that can be treated using cardiac ablation is atrial fibrillation (AF), which is an abnormal heart rhythm that originates in the atria of the heart. Goals of cardiac ablation are to remove the arrhythmia to return the patient's heart to a normal heart rhythm or reduce the frequency of arrhythmia and the severity of symptoms in the patient.

Cardiac ablation may employ long, flexible catheters (endoscope) that may be inserted through a small incision in the groin and through the blood vessels to the heart, and may be used to apply energy (e.g., radio frequency (RF) energy, or extreme cold) to produce small scars or lesions on the tissue to block faulty electrical impulses that may cause the heart rhythm disorders. These lesions, also called transmural lesions, are scar tissue that penetrates the heart tissue and keeps errant electrical signals from being transmitted. The goal of any cardiac ablation procedure is to create a transmural lesion while minimizing complications.

Proper positioning of the distal end of the catheter is of critical importance so that a precise application of radio frequency (RF) energy is delivered to the specified location or series of locations, as determined by diagnostics. Precise positioning of the probe is also important in diagnostic and mapping procedures that are performed in advance of such a medical procedure to determine the specific area of the heart requiring treatment. However, current medical systems only provide visual modalities for guidance during cardiac ablation procedures.

Described herein is an auditory guidance system and method for medical systems and procedures. The auditory guidance system provides non-visual indications to operator(s) of the operational status with respect to a number of operational parameters during a medical, diagnostic or mapping procedure, for example.

Figure 1:
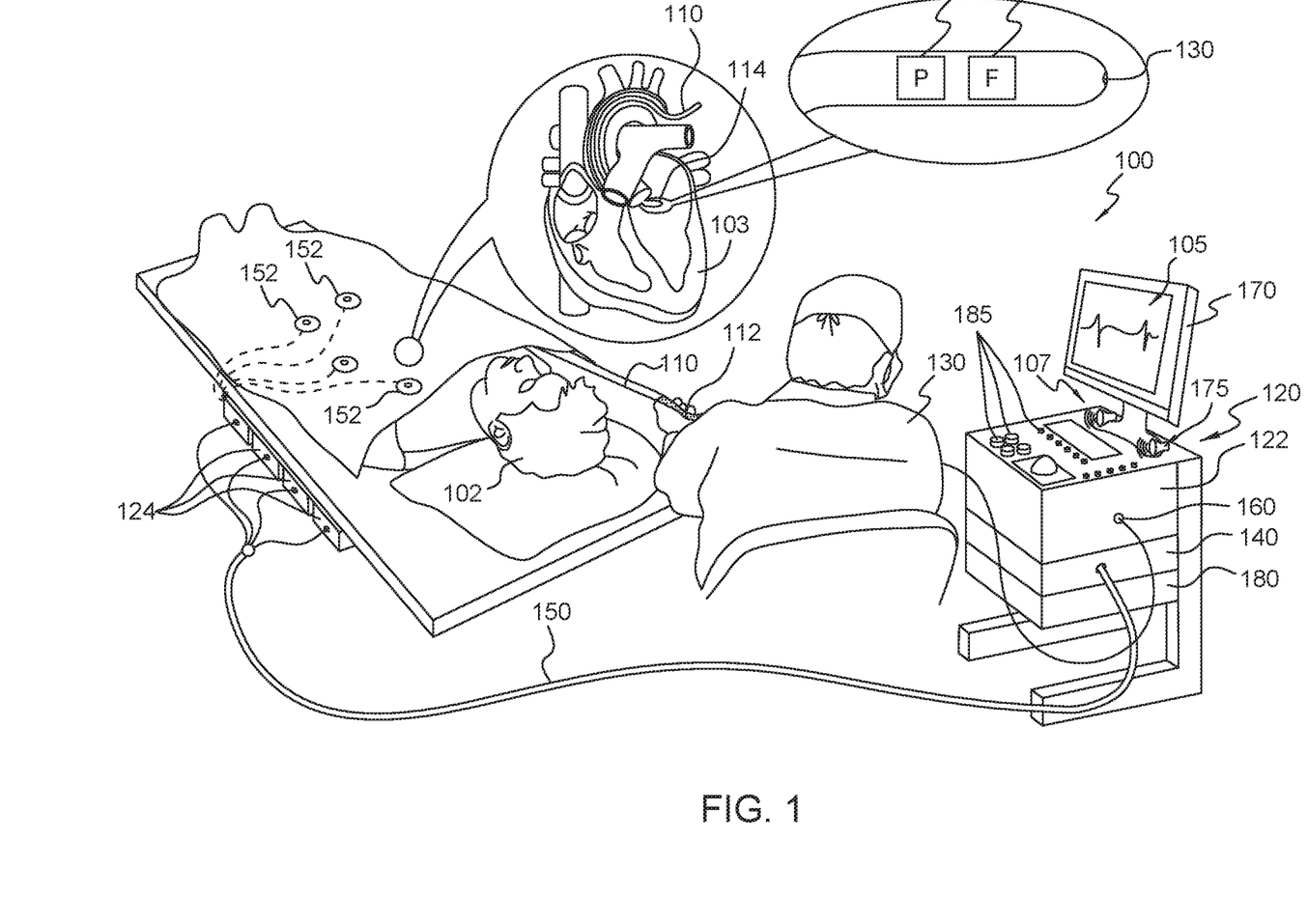
FIG. 1 is a high level schematic, pictorial illustration of a medical system in accordance with certain implementations.

FIG. 1 is a high level illustration of an example medical system 100 that is used to generate and display information 105 and provide audio guidance signals 107, (some of which are based on information 105), during a medical procedure and to control the deployment of various probes within a subject. Example system 100 includes a probe 110, such as an intracardiac catheter, a console 120 and an associated probe control unit 112. As described herein, it will be understood that probe 110 is used for diagnostic or therapeutic treatment, such as for example, mapping electrical potentials in a heart 103 of a patient 102 or performing an ablation procedure. Alternatively, probe 110 can be used, mutatis mutandis, for other therapeutic and/or diagnostic purposes in heart 103, lungs, or in other body organs and ear, nose, and throat (ENT) procedures.

An operator 130 can, for example, insert probe 110 into the vascular system of patient 102 using probe control unit 112 so that a distal end 114 of probe 110 enters a chamber of the patient's heart 103. Console 210 can use magnetic position sensing to determine position coordinates of distal end 114 inside heart 103. To determine the position coordinates, a driver circuit 122 in console 120 may drive field generators 124 to generate magnetic fields within the body of patient 102. Field generators 124 can include coils that may be placed below the torso of the patient 103 at known positions external to patient 103. These coils may generate magnetic fields in a predefined working volume that contains heart 103.

A location sensor 126 within distal end 114 of probe 110 can generate electrical signals in response to these magnetic fields. A signal processor 140 can process these signals in order to determine the position coordinates of distal end 114, including both location and orientation coordinates. Known methods of position sensing described hereinabove are implemented in the CARTO™ mapping system produced by Biosense Webster Inc., of Diamond Bar, Calif., and is described in detail in the patents and the patent applications cited herein.

Location sensor 126 is configured to transmit a signal to console 120 that is indicative of the location coordinates of distal end 114. Location sensor 126 can include one or more miniature coils, and typically can include multiple coils oriented along different axes. Alternatively, location sensor 126 can comprise either another type of magnetic sensor, or position transducers of other types, such as impedance-based or ultrasonic location sensors.

Probe 110 can also include a force sensor 128 contained within distal end 114. Force sensor 128 can measure a force applied by distal end 114 to the endocardial tissue of heart 103 and generate a signal that is sent to console 120. Force sensor 128 can include a magnetic field transmitter and a receiver connected by a spring in distal end 114, and can generate an indication of the force based on measuring a deflection of the spring. Further details of this type of probe and force sensor are described in U.S. Patent Application Publications 2009/0093806 and 2009/0138007, and are incorporated herein by reference as if fully set forth. Alternatively, distal end 114 can include another type of force sensor that can use, for example, fiber optics or impedance measurements.

Probe 110 can include an electrode 130 coupled to distal end 114 and configured to function as an impedance-based position transducer. Additionally or alternatively, electrode 130 can be configured to measure a certain physiological property, for example the local surface electrical potential of the cardiac tissue at one or more of the multiple locations. Electrode 130 can be configured to apply radio frequency (RF) energy to ablate endocardial tissue in heart 103.

Although example medical system 100 can be configured to measure the position of distal end 114 using magnetic-based sensors, other position tracking techniques can be used (e.g., impedance-based sensors). Magnetic position tracking techniques are described, for example, in U.S. Pat. Nos. 5,391,199, 5,443,489, 6,788,967, 6,690,963, 5,558,091, 6,172,499, and 6,177,792, and are incorporated herein by reference as if fully set forth. Impedance-based position tracking techniques are described, for example, in U.S. Pat. Nos. 5,983,126, 6,456,864 and 5,944,022, and are incorporated herein by reference as if fully set forth.

Signal processor 140 can be included in a general-purpose computer, with a suitable front end and interface circuits for receiving signals from probe 110 and controlling the other components of console 120. Signal processor 140 can be programmed, using software, to carry out the functions that are described herein. The software can be downloaded to console 120 in electronic form, over a network, for example, or it can be provided on non-transitory tangible media, such as optical, magnetic or electronic memory media. Alternatively, some or all of the functions of signal processor 140 can be performed by dedicated or programmable digital hardware components.

In the example of FIG. 1, console 120 can also be connected by a cable 150 to external sensors 152. External sensors 152 can include body surface electrodes and/or position sensors that can be attached to the patient's skin using, for example, adhesive patches. The body surface electrodes can detect electrical impulses generated by the polarization and depolarization of cardiac tissue. The position sensors can use advanced catheter location and/or magnetic location sensors to locate probe 110 during use. Although not shown in FIG. 1, external sensors 152 can be embedded in a vest that is configured to be worn by patient 102. External sensors 152 can aid in identifying and tracking the respiration cycle of patient 103. External sensors 152 can transmit information to console 120 via cable 150.

Additionally, or alternatively, probe 110, and external sensors 152 can communicate with console 120 and one another via a wireless interface. For example, U.S. Pat. No. 6,266,551, whose disclosure is incorporated herein by reference, describes, inter alia, a wireless catheter, which is not physically connected to signal processing and/or computing apparatus. Rather, a transmitter/receiver is attached to the proximal end of the catheter. The transmitter/receiver communicates with a signal processing and/or computer apparatus using wireless communication methods, such as infrared (IR), radio frequency (RF), wireless, Bluetooth®, acoustic or other transmissions.

Probe 110 can be equipped with a wireless digital interface that can communicate with a corresponding input/output (I/O) interface 160 in console 120. Wireless digital interface and the I/O interface 160 can operate in accordance with any suitable wireless communication standard that is known in the art, such as IR, RF, Bluetooth, one of the IEEE 802.11 families of standards, or the HiperLAN standard. External sensors 152 can include one or more wireless sensor nodes integrated on a flexible substrate. The one or more wireless sensor nodes can include a wireless transmit/receive unit (WTRU) enabling local digital signal processing, a radio link, and a power supply such as miniaturized rechargeable battery.

Wireless digital interface and the I/O interface 160 can enable console 120 to interact with probe 110 and external sensors 152. Based on the electrical impulses received from external sensors 152 and signals received from probe 110 via Wireless digital interface and the I/O interface 160 and other components of medical system 100, signal processor 140 can generate information 105 which can be shown on a display 170, and/or audio guidance signals which can output on speakers 175.

In an example, signal processor 140 can also provide audio guidance signals 107 based on information 105, which can be provided via audio devices, such as speakers 175, headphones, wireless headphones and/or other similar devices. In general, audio guidance signals 107 are operator selected songs, where different musical elements are paired to different parameters of a procedure or to different parts of the procedure itself. The musical elements in the selected song or the song itself can be played differently or be modified in some manner depending on differences between information 105 and predetermined thresholds for the parameters. This is described in greater detail herein below.

In another example, audio guidance signals 107 can include sound effects that can be used to assist the operator in determining how much to ablate. These sound effects, such as tempos, volumes and frequencies can be mapped to width and depth of an ablation target to enable the operator to achieve a transmural lesion in confidence. The sound effects are varied as the operator moves from an edge to a center and back to another edge. This is described in greater detail herein below.

In another example, audio guidance signals 107 can be use during a mapping process. For example, as an operator maps an ablation target, sounds effects are added to the mapping data. This allows the operator to better understand when an area has already been mapped and that it is time to move to the next site.

During the diagnostic treatment, signal processor 140 can present information 105, broadcast audio guidance signals 107 and/or can store data representing information 105 or audio guidance signals 107 in a memory 180. Memory 180 can include any suitable volatile and/or non-volatile memory, such as random access memory or a hard disk drive.

Probe control unit 112 can be configured to be operated by an operator 130 to manipulate probe 110 based on information 105 or audio guidance signals 107 which is selectable using one or more input devices 185. Alternatively, medical system 100 can include a second operator that manipulates console 120 while operator 130 operates probe control unit 112 to manipulate probe 110 based on information 105 or audio guidance signals 107. The second operator can also be provided with information 105 or audio guidance signals 107. The mechanics of the construction and use of probe control device 112 to move and position distal end 114 of probe 110 is within the state of the art such as employed in the CARTO™ mapping system referenced above. For example, see also U.S. Pat. No. 6,690,963 which is incorporated herein by reference as if fully set forth.

Figure 2:
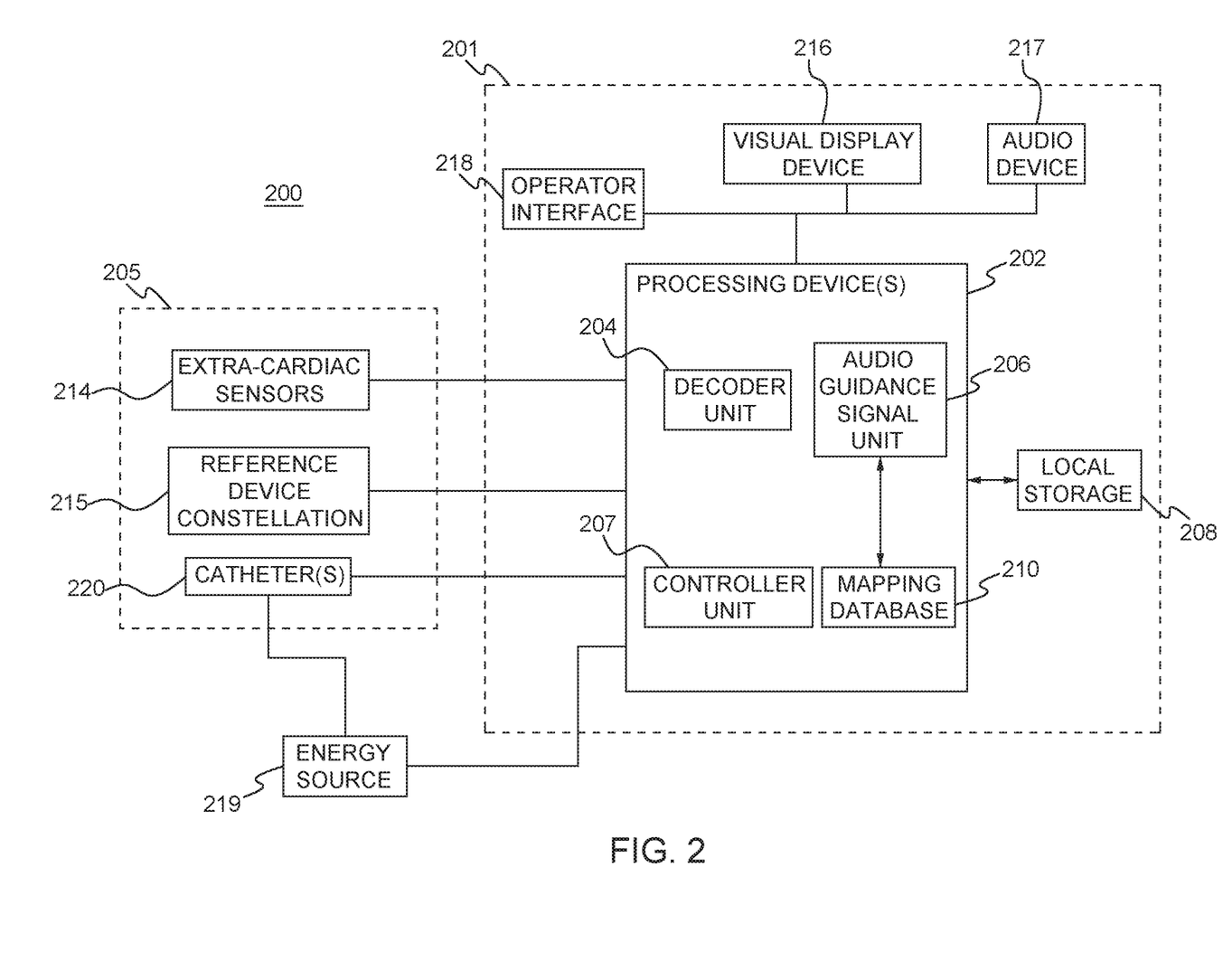
FIG. 2 is a detailed schematic diagram of an example medical system in accordance with certain implementations.

FIG. 2 is a more detailed schematic diagram of an example medical system 200 which incorporates a system and method for auditory guidance. Medical system 200, which may be for illustration purposes, a cardiac mapping and ablation system, may include, but is not limited to, any of the following components: a console system 201; extra-cardiac sensors 214; reference device constellation 215; energy source 219; and/or catheter(s) 220.

Console system 201 may include, but is not limited to include, any of the following components: processing device(s) 202 (processor(s)); local storage 208; visual display device 216; audio device 217 and/or operator interface(s) 218. Audio device 217 can be, but is not limited to, speakers, headphones, or wireless headphones, and can be provided to one or more operators of medical system 200. Certain elements of medical system 200 may be used directly on, in, and/or in proximity to patient 205 in order to gather information to be used for visualization, audio guidance signaling, diagnostics, and to perform ablation therapy. This information may be provided to console system 201 for processing, visualization, audio guidance signaling and operator control and direction, some of which is described below.

Operator interface(s) 218 may be used by one or more operators to interact with and control medical system 200. Operator interface(s) 218 may include, but are not limited to include, the following devices: a keyboard; a touch-sensitive display; and/or a mouse. Operator interface(s) 218 may allow operators to access and manipulate visual information, and may provide them with the ability to change views, increase/decrease audio from audio device 217 and tag and/or label lesions to keep track of treatment strategies for individual patients. Operators of medical system 200 may include, but are not limited to include, the following: a physician (e.g., an electrophysiologist) who may, for example, control the catheter, gather and interpret diagnostics, and perform the ablation procedure; and a Clinical Application Specialist (CAS) who functions as the physician's assistant during the procedures.

Reference device constellation 215 (e.g., may be referred to as a location pad) may include a ring of computer-controlled (e.g., controlled by processing device(s) 202) magnets positioned beneath the patient 205. The magnets may have known and fixed strength and position values that may be used as point of origin references for the magnetic fields in the surrounding space and may provide the reference information to processing device(s) 202 to be used in producing accurate 3D images of the heart.

Extra-cardiac sensor(s) 214 may be electrodes on the skin of a patient 205, for example. Extra-cardiac sensor(s) 214 may detect the electrical activity of the heart via detection of electrical changes on the skin due to the electro-physiologic pattern of the heart, and provide information on the electrical activity to processing device(s) 202 to be used in diagnosing arrhythmias and determining a therapeutic course of action. Processed versions of the extra-cardiac signals detected by extra-cardiac sensor(s) 214 may be displayed on visual display device 216, for example in a graphical user interface (GUI), and may be used to generate audio guidance signals to operators via audio device 217.

One or more devices may be used on patient 205 for therapeutic and diagnostic purposes. In example medical system 200, catheter(s) 220 are shown and described for these purposes; however, other devices may be used for diagnostics and/or therapeutic treatment.

One or more catheter(s) 220 may be percutaneously inserted by a physician through the patient's 205 vascular system into the heart of the patient 205. Catheter(s) 220 may be equipped with a variety of sensors, such as location, electrical, pressure, image and/or temperature sensors, for the purpose of gathering information for diagnostic mapping and/or delivering therapeutic treatment (e.g., performing ablation). Different types of catheter(s) 220 may be used including, but not limited to, the following example types: fixed catheter; deflectable catheter; bi-directional catheter; uni-directional catheter; tricuspid mapping catheter; halo-shaped tip catheter; basket catheter; and/or lasso-shaped catheter. When catheter(s) 220 is used for performing ablation on a target location (e.g., one or more locations along a path), for example by applying RF energy, catheter(s) 220 may receive the RF energy from energy source 219, as may be instructed by processing device(s) 202. In an example, catheter(s) 220 may request the RF energy directly from energy source 219.

Figure 3:
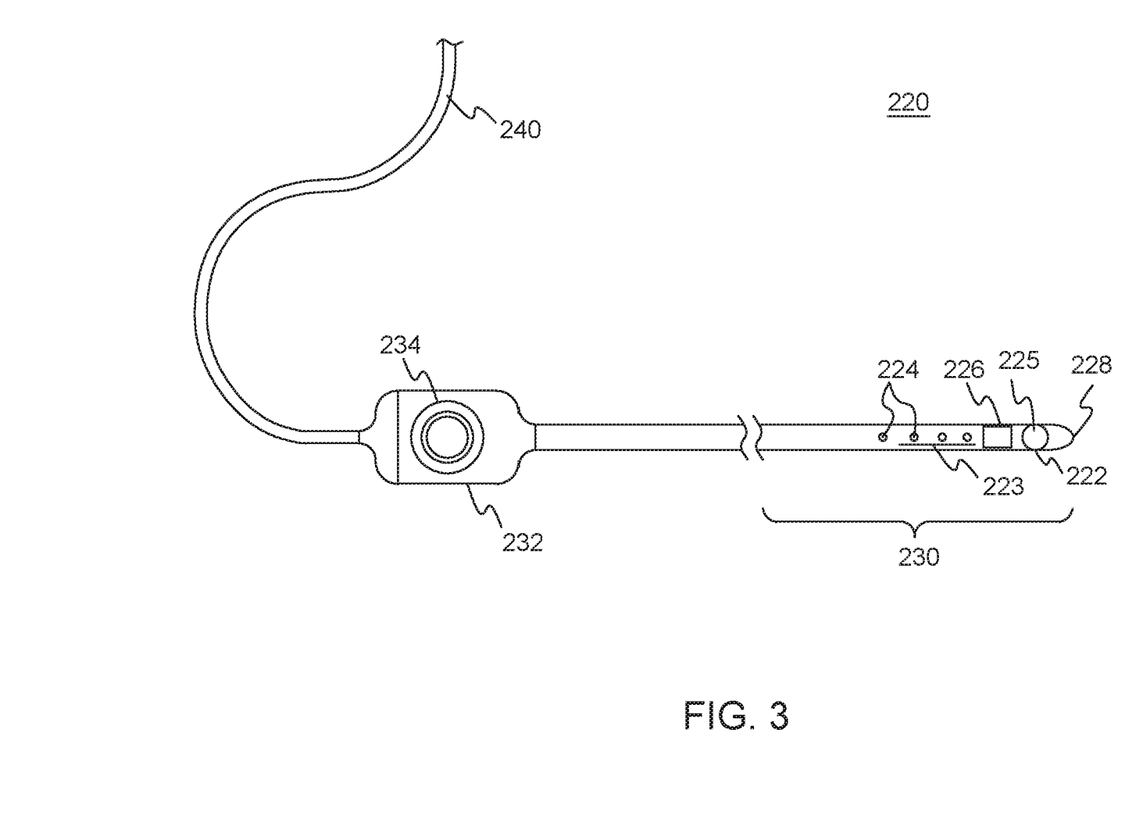
FIG. 3 is a schematic diagram of an example catheter that may be included in the example medical system of FIG. 2 in accordance with certain implementations.

An example catheter 220 is shown in greater detail in FIG. 3, showing some, but not all, of the elements that may be included in catheter 220. A catheter 220 may include, but is not limited to include, any one or more of the following components: electrode(s) 222; temperature sensor(s) 223; non-contact electrodes 224; image sensor(s) 225; positioning sensor(s) 226; distal tip 228; distal end 230; handle 232; and/or cable 240. The schematic diagram of catheter 220 in FIG. 3 is a high-level representation of possible components of catheter 220, such that the location and configuration of the components in catheter 220 may be different than shown.

Distal end 230 of catheter 220 may include an electrode(s) 222 at distal tip 228 that may be used to measure electrical properties of the cardiac tissue. Electrode(s) 222 may also be used to send electrical signals to the heart for diagnostic purposes. Electrode(s) 222 may also perform ablation on defective cardiac tissue by applying energy (e.g., RF energy) directly to the cardiac tissue at the desired location of ablation.

Distal end 230 of catheter 220 may include temperature sensor(s) 223 to measure the temperature of the cardiac tissue in contact with distal end 230 and/or measure the temperature of distal end 230 itself. For example, thermocouples or thermistors for measuring temperature may be placed anywhere along distal end 230 to serve as temperature sensor(s) 223.

Distal end 230 may include non-contact electrodes 224 arranged in an array, which may be used to simultaneously receive and measure far-field electrical signals from the walls of the heart chamber of patient 205. Electrode(s) 222 and non-contact electrodes 224 provide information regarding the electrical properties of the heart to processing device(s) 202 for processing.

Catheter(s) 220 may be equipped with one or more image sensor(s) 225, such as a charge coupled device (CCD) image sensor, and/or a camera for capturing endoscopic images when inserted in a body cavity. Image sensor(s) 225 may be located at distal end 230.

Distal end 230 may include positioning sensor(s) 226 (also called location sensors) in distal tip 228 of catheter 220 that may generate signals used to determine the position and orientation (and/or distance) of catheter 220 in the body. In an example, the relative position and orientation of positioning sensor(s) 226, electrode(s) 222, and distal tip 228 are fixed and known in order to facilitate accurate positioning information of distal tip 228. For example, the position of positioning sensor(s) 226 may be determined in part based on the relative position to known positions outside the heart (e.g., based on extra-cardiac sensors 214). The use of positioning sensor(s) 226 may provide improved location accuracy within the magnetic fields in the surrounding space and provide location information that is adaptable to patient movement because the position information of catheter 220 is relative to the anatomy of patient 205.

Handle 232 of catheter 220 may be operated by a physician and may include controls 234 to enable the physician to effectively steer distal tip 228 in the desired direction.

Electrodes 222, 224, and sensors 223, 225, 226 may be connected to processing device(s) 202 via wires that may pass through handle 232 and cable 240, in order to provide information, such as location, electrical, imaging and/or temperature information, to console system 201, which may be used to operate and display the function of catheter 220 within the heart in real-time, and provide audio guidance signals to an operator.

With reference now to FIG. 2, within console system 201, processing device(s) 202 (e.g., processor(s)) may include one or more signal processing circuits that may be contained inside a computer, for example. Processing device(s) 202 may be implemented in hardware and/or programmed in software to carry out the functions of medical system 200. This software may be downloaded to processing device(s) 202 in electronic form, over a network, for example, and/or it may be provided on tangible media, such as magnetic or optical media or other nonvolatile memory. For example, enhancements may be made to the audio guidance system of medical system 200 by downloading and installing software modules to processing device(s) 202. In an example, processing device(s) 202 may comprise a general-purpose computer.

Processing device(s) 202 may receive, amplify, filter and/or digitize signals (carrying information or data) from catheter 220, including signals generated by sensors 223, 225, and 226, and electrodes 222 and 224. The signals are received and used by processing device(s) 202 to compute such data as the position and orientation of catheter 220, the temperature of catheter 220, as well as the electrical characteristics and/or temperature of tissues in the heart chamber. In an example, appropriate circuitry may be associated with catheter 220 itself so that processing device(s) 202 receive signals that are already amplified, filtered and/or digitized.

Processing device(s) 202 may also be used to generate and send signals, containing information or instructions, to other elements in medical system 200. For example, processing device(s) 202 may generate and send audio guidance signals to audio device 217. In another example, processing device(s) 202 may send/receive information to/from local storage 208. In another example, processing device(s) 202 may send signals to catheter(s) 220 to apply RF energy provided by energy source 219 to an ablation target.

As explained above, processing device(s) 202 may implement specific functions, which may be represented (e.g., illustratively or physically) as separate units within processing device(s) 202. For example, processing device(s) 202 may include a decoder unit 204 (e.g., implemented in hardware as a processing circuit and/or software as a software module) that may be configured to receive signals from sensors in catheter 220, and may use the signals to calculate position, orientation, distance, temperature and/or electrocardiogram (ECG) values for distal tip 228.

In another example, processing device(s) 202 may include a controller unit 207 for sending instructions to other devices in medical system 200. For example, controller unit 207 may send instructions to energy source 219 to provide RF energy to catheter(s) 220 for ablation, and may send instructions to catheter(s) 220 to apply the RF energy to an ablation target (e.g., one or more locations along a path).

In another example, the processing device(s) 202 may include an audio guidance signal unit 206 (e.g., implemented in hardware as processing circuits and/or software as a software module). Audio guidance signal unit 206 may be connected to operator interface 218 for receiving a song selection from an operator, such as a physician, and procedure and/or parameter mapping information. Songs may be stored and selected from local storage 208, for example. Other memory devices may be utilized. The procedure and/or parameter mapping information may be stored in mapping database 210, local storage 208 or other appropriate memory devices. Audio guidance signal unit 206 may be connected to audio device 217 for outputting the audio guidance signals.

In general, audio guidance signal unit 206 may be configured to collect parameter information from the sensors described herein, including but not limited to, location, electrical, pressure, and/or temperature sensors. A mapping database 210 may be configured to store relationships between an operator selected song and different parameters. Audio guidance signal unit 206 may be configured to compare the parameter information against predetermined thresholds for each parameter, modify the physician selected song in accordance with the comparisons using mapping database 210, and output the audio guidance signals via audio device 217. The modified song represents a different modality from which the physician can determine procedure performance in real-time without having to look at visual display device 216.

Audio guidance signal unit 206 may also be configured to collect parameter information from the sensors described herein related to the depth and width of an ablation target. Mapping database 210 may be configured to store relationships between sound effects and the depth and width of an ablation target. Audio guidance signal unit 206 may be configured to compare the parameter information against the depth and width of an ablation target, modify the sound effects accordingly and output the audio guidance signals via audio device 217. For example, the sound effects are varied as the operator moves from an edge to a center and back to another edge.

Audio guidance signal unit 206 may also be used during the mapping process. For example, as an operator maps an ablation target, sounds effects are added to the mapping data and stored, for example, in mapping database 210 or local storage 208. Audio guidance signal unit 206 may be configured to compare parameter information, such as the location of catheter or probe against already mapped ablation targets, and output a sound effect via audio device 217 to alert the operator. This allows the operator to better understand when an area has already been mapped and that it is time to move to the next site.

Processing units 204, 206 and 207 are examples, and do not comprise all the possible functions that may be implemented in processing device(s) 202. Other functionality and/or processing units may be included in processing device(s) 202 but are not shown.

As described herein above, audio device 217 may be used to play audio guidance signals provided by audio guidance signal unit 206. Audio device 217 may include but is not limited to, speakers at console 201, physician headsets and secondary operator headsets.

Visual display device 216 may be used to display 2D and/or 3D visual representations and/or maps of the heart and show the exact location and orientation of the catheter 220 within the heart, based on information processing done in the processing device(s) 202. For example, maps may be displayed as anatomical maps, cardiac electrical activation maps, cardiac electrical propagation maps, cardiac electrical potential maps, impedance maps, cardiac chamber geometry, and ECG fragmentation maps. In addition to the cardiac representations/maps and catheter(s), other objects in view and/or information (e.g., labels, diagnostics etc.) relevant to the mapping, diagnostic and therapeutic procedures may also be displayed on visual display device 216.

Figure 4:
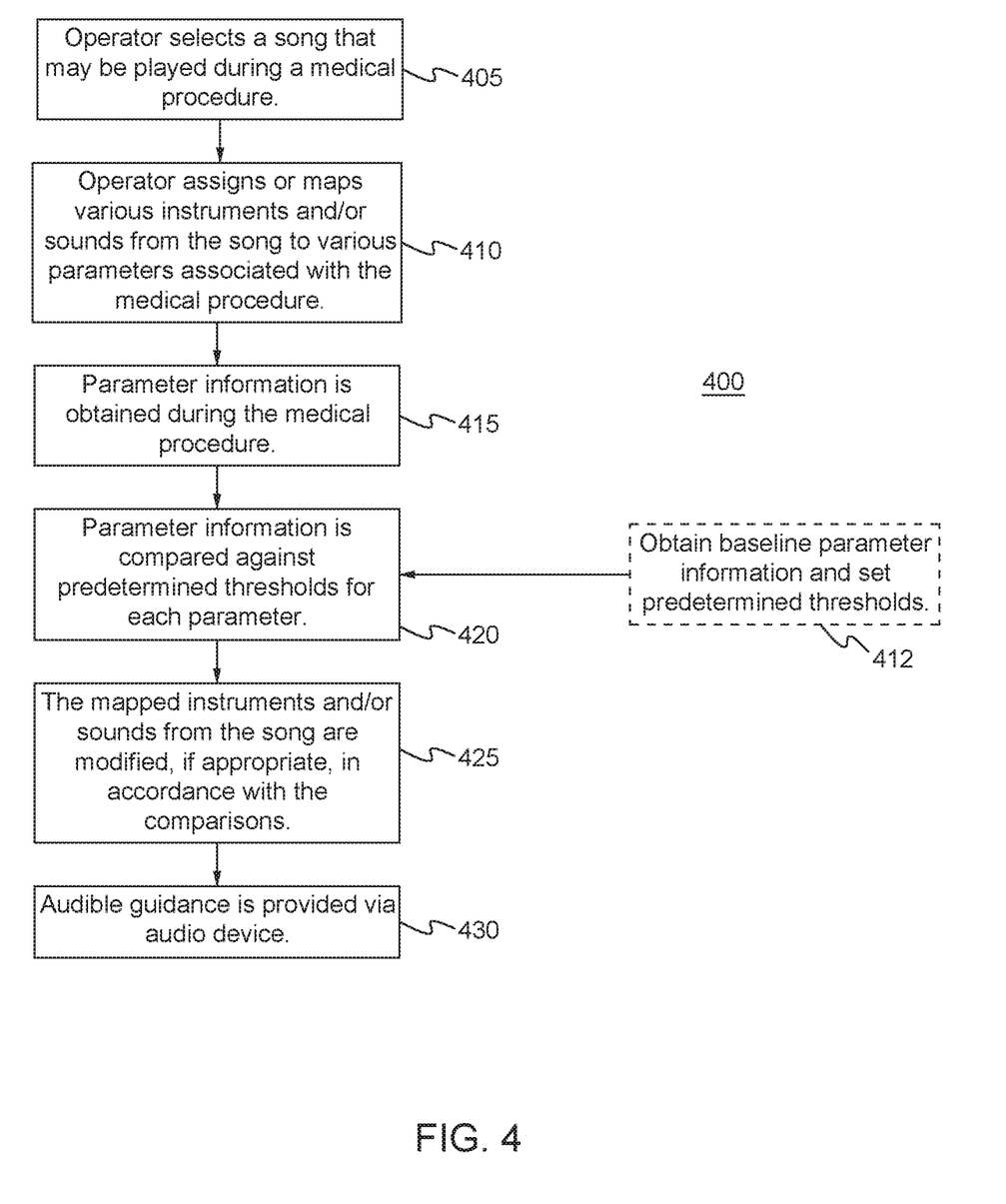
FIG. 4 is a flow diagram of an example auditory guidance method in accordance with certain implementations that may be used in the example medical system of FIG. 1 and FIG. 2 in accordance with certain implementations.

FIG. 4 is a flow diagram 400 of an example auditory guidance method in accordance with certain implementations that may be used in the example medical system of FIGS. 1 and/or 2 in accordance with certain implementations. An operator, for example a physician, selects a song that may be played during a medical or diagnostic procedure (collectively referred to as medical procedure) (405). The songs may be stored in variety of memory or storage devices, such as, local storage 208. In an example, the physician assigns or maps various instruments and/or sounds from the song to various parameters associated with the medical procedure (410). The parameters can include, but are not limited to, location, electrical, pressure, and/or temperature. The mapping information may be stored in a table, for example, in mapping database 210 or in a variety of other relational structures or memory devices.

Parameter information is obtained during the medical procedure (415). The parameter information is compared against predetermined thresholds for each parameter (420). The predetermined thresholds may be stored in a table, for example, in mapping database 210, local storage 208, or in a variety of other structures or memory devices. In an example, predetermined thresholds may be set by obtaining baseline parameter information prior to the actual medical procedure and setting maximum and minimum values for each parameter relative to the baseline parameter information (412). The mapped instruments and/or sounds from the song are modified, if appropriate, in accordance with the comparisons (425). Modifications may include, but are not limited, changing tempo, frequency and other similar elements that result in recognizable deviations or differences in the song. The modified song is then output using, for example, audio device 217 or speaker 175 (430).

Figure 5:
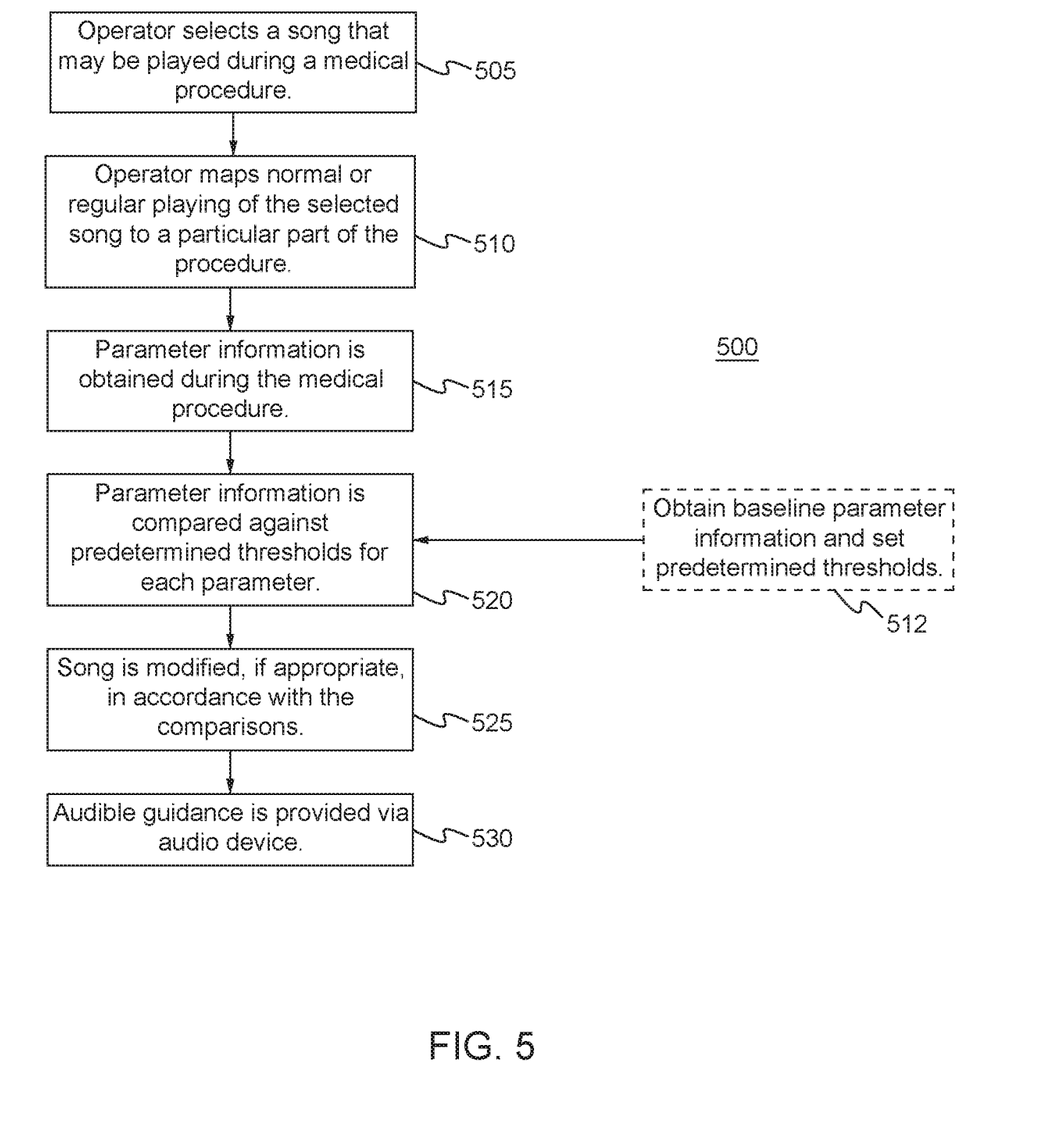
FIG. 5 is a flow diagram of another example auditory guidance method in accordance with certain implementations that may be used in the example medical system of FIG. 1 and FIG. 2 in accordance with certain implementations.

FIG. 5 is a flow diagram 500 of an example auditory guidance method in accordance with certain implementations that may be used in the example medical system of FIGS. 1 and/or 2 in conjunction with the method of FIG. 4 in accordance with certain implementations. An operator, for example a physician, selects a song that may be played during a medical or diagnostic procedure (collectively referred to as medical procedure) (505). The songs may be stored in variety of memory or storage devices, such as, local storage 208. In an example, the physician assigns or maps normal or regular playing of the selected song to a particular part of the procedure (510). For example, the song is played in regular mode if the patient is in sinus rhythm and non-regular mode if in arrhythmia. The mapping information may be stored in a table, for example, in mapping database 210 or in a variety of other relational structures or memory devices.

Parameter information that is indicative of the selected part of the procedure is obtained during the medical procedure (515). The parameter information is compared against predetermined thresholds for each parameter (520). The predetermined thresholds may be stored in a table, for example, in mapping database 210, local storage 208, or in a variety of other structures or memory devices. In an example, predetermined thresholds may be set by obtaining baseline parameter information prior to the actual medical procedure and setting maximum and minimum values for each parameter based on a norm for the selected part of the procedure (512). The song is modified, if appropriate, in accordance with the comparisons (525). Modifications may include, but are not limited, changing tempo, frequency and other similar elements that result in recognizable deviations or differences in the song, i.e., becomes un-harmonized. The modified song is then output using, for example, audio device 217 or speaker 175 (530).

Figure 6:
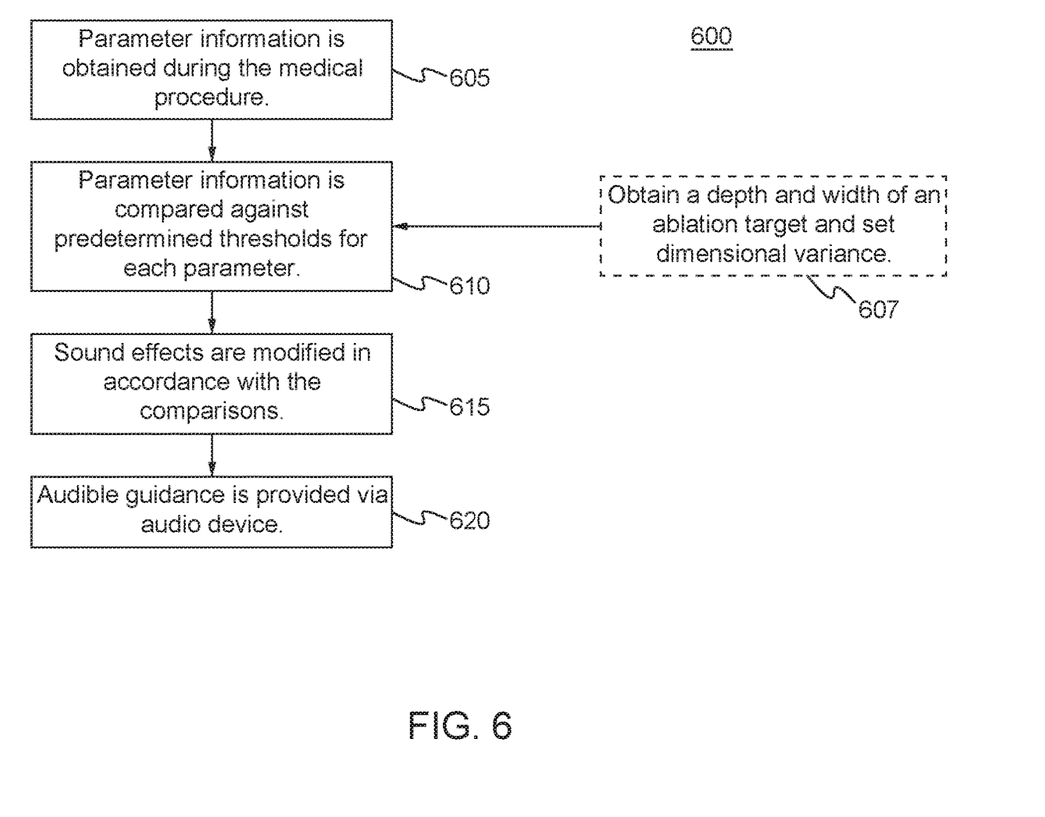
FIG. 6 is a flow diagram of yet another example auditory guidance method that may be used in the example medical systems of FIG. 1 and FIG. 2 and in conjunction with the methods of FIG. 4 and FIG. 5 in accordance with certain implementations.

FIG. 6 is a flow diagram 600 of yet another example auditory guidance method that may be used in the example medical systems of FIG. 1 and/or FIG. 2 and/or in conjunction with the methods of FIG. 4 and/or FIG. 5 in accordance with certain implementations. Parameter information that is indicative of the depth and width of an ablation target, for example, is obtained during the medical procedure (605). The parameter information is compared against predetermined thresholds for each parameter (610). The predetermined thresholds may be stored in a table, for example, in mapping database 210, local storage 208, or in a variety of other structures or memory devices. In an example, predetermined thresholds may be set by obtaining a depth and width of an ablation target prior to the actual medical procedure and setting edge to center values or similar dimensional variance for each parameter (607). The sound effects are modified, if appropriate, in accordance with the comparisons (615). Modifications may include, but are not limited, changing tempo, frequency and other similar elements that result in recognizable deviations or differences in the sound effects, e.g., fast to slow, or absence of sound. The modified song is then output using, for example, audio device 217 or speaker 175 (620).

Figure 7:
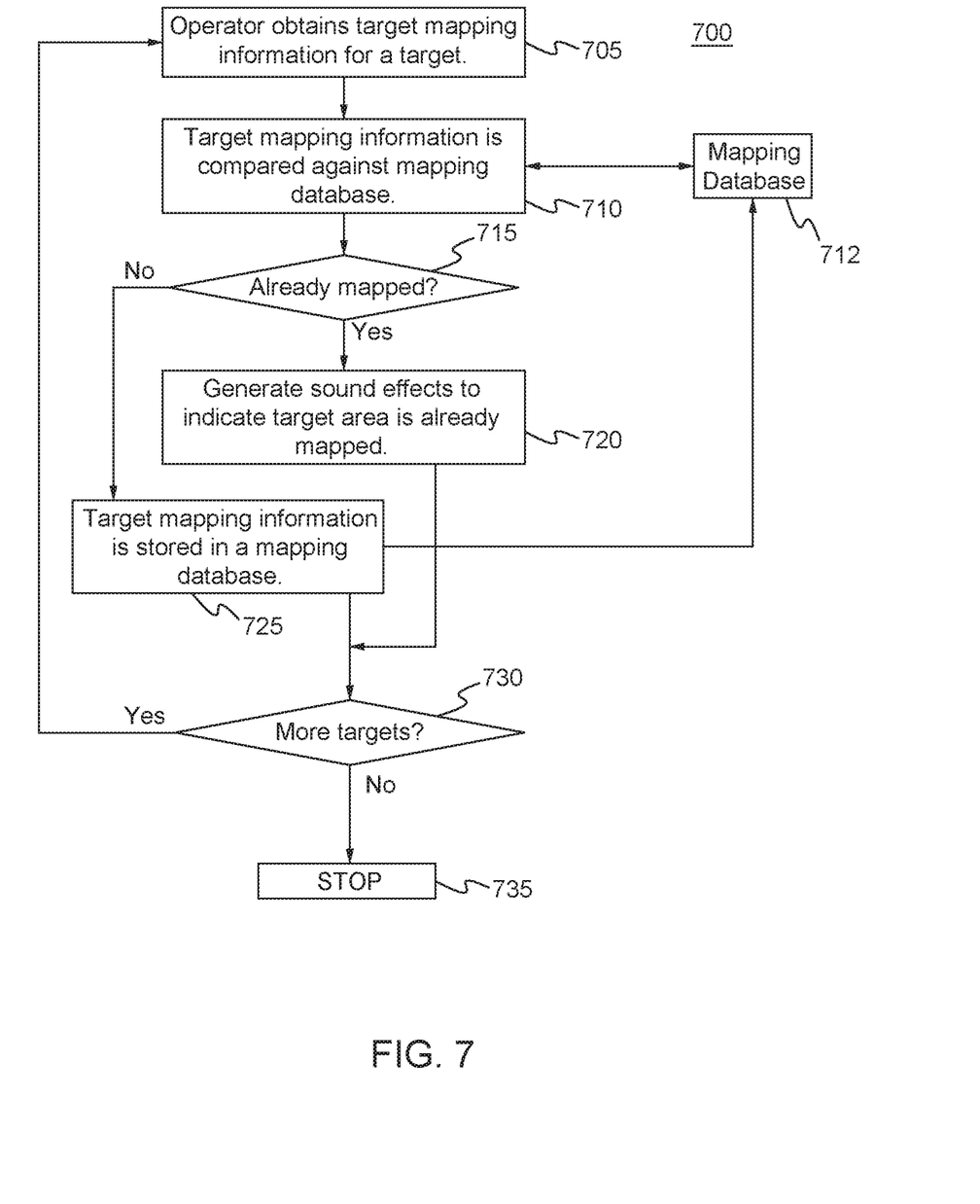
FIG. 7 is a flow diagram of an example auditory guidance method for mapping that may be used in the example medical system of FIG. 1 and FIG. 2 and in conjunction with the methods of FIG. 4, FIG. 5 and FIG. 6 in accordance with certain implementations.

FIG. 7 is a flow diagram 700 of an example auditory guidance method for mapping that may be used in the example medical systems of FIG. 1 and/or FIG. 2 and/or in conjunction with the methods of FIG. 4, FIG. 5 and/or FIG. 6 in accordance with certain implementations. Operator obtains target mapping information for an ablation target (705). Target mapping information is compared against mapping database 712 (710). A determination is made as to whether the ablation target is already mapped (715). If yes, sound effects are generated to indicate to the operator that the ablation target has already been mapped (720). A determination is then made as to whether there are any additional ablation targets (730). If yes, operator obtains the target mapping information for another ablation target (705). If no further targets, method completes (735). If the target mapping information is not in mapping database 712, then the target mapping information is stored in mapping database 712 (725). A determination is then made as to whether there are any additional ablation targets (730). If yes, operator obtains the target mapping information for another ablation target (705). If no further targets, method completes (735).

In general, a method for providing auditory guidance during a medical procedure includes selecting a song for playing during the medical procedure and assigning at least a portion of the song to the medical procedure. Parameter information is obtained for at least one parameter associated with the medical procedure during the medical procedure and compared against predetermined thresholds for each parameter. The at least a portion of the song is modified in accordance with the comparison and played to provide auditory guidance. In an implementation, the assigning includes assigning instruments from the song to parameters associated with the medical procedure. In an implementation, an audible characteristic of an instrument is modified in accordance with the comparison. In an implementation, the assigning includes assigning sounds from the song to parameters associated with the medical procedure. In an implementation, an audible characteristic of a sound is modified in accordance with the comparison. In an implementation, the method further includes obtaining baseline parameter information and setting predetermined thresholds using the baseline parameter information. In an implementation, the assigning includes assigning a mode of playing of the song to at least a portion of the medical procedure. In an implementation, the mode of playing the song is modified in accordance with the comparison. In an implementation, different modes of playing are associated with different portions of the medical procedure. In an implementation, the parameter is a depth and width of an ablation target and the predetermined threshold is a dimensional variance of the depth and the width of the ablation target. In an implementation, the parameter is target mapping information of an ablation target and the predetermined threshold is a presence or absence of the ablation target in a target mapping database.

In general, a system for providing auditory guidance during a medical procedure includes a mapping database configured to at least store relationships between at least a portion of a user selected song and the medical procedure, and an audio guidance signal unit configured to obtain parameter information for at least one parameter associated with the medical procedure during the medical procedure. The audio guidance signal unit is configured to compare the obtained parameter information against predetermined thresholds for each parameter stored in the mapping database and is configured to modify the at least a portion of the song in accordance with the comparison. An audio device is configured to play the modified portion of the song to provide auditory guidance. In an implementation, the instruments from the user selected song are mapped to parameters associated with the medical procedure. In an implementation, the audio guidance signal unit is configured to modify an audible characteristic of an instrument in accordance with the comparison. In an implementation, sounds from the user selected song are mapped to parameters associated with the medical procedure. In an implementation, the audio guidance signal unit is configured to modify an audible characteristic of a sound in accordance with the comparison. In an implementation, the mapping database is configured to store baseline parameter information and predetermined thresholds. In an implementation, a playing of the user selected song is mapped to at least a portion of the medical procedure. In an implementation, the audio guidance signal unit is configured to modify the playing of the song in accordance with the comparison. In an implementation, the parameter is a depth and width of an ablation target and the predetermined threshold is a dimensional variance of the depth and the width of the ablation target.

The description herein is with respect to cardiac mapping and ablation procedures for a cardiac system, although it is understood by one skilled in the art that the disclosures may be applied to systems and procedures that can be used in any cavity or system in the body, including, but not limited to, the respiratory/pulmonary system, the respiratory and pulmonary system, the digestive system, the neurovascular system, and/or the circulatory system.

The embodiments and procedures described herein may be implemented in hardware, and/or software. A computer system for performing ablation may be capable of running software modules that introduce additional features including the procedures described herein. The procedures described herein may enable advanced audio guidance signaling, and diagnostic capabilities to enhance clinicians' ability to diagnose and treat heart rhythm disorders. Although the procedures disclosed herein are describe with respect to ablation procedures relating to a cardiac system, the systems and procedures disclosed herein may be similarly used as part of therapeutic and diagnostic procedures in other parts of the body.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A system for providing auditory guidance during a medical procedure, the system comprising:
 a mapping database configured to store relationships between a portion of a user selected song and the medical procedure;
 an audio guidance signal unit configured to continuously play the user selected song during at least a portion of the medical procedure;
 the audio guidance signal unit configured to obtain parameter information for at least one parameter associated with the medical procedure during the medical procedure;
 the audio guidance signal unit configured to compare the obtained parameter information against predetermined thresholds for each parameter stored in the mapping database;
 the audio guidance signal unit configured to modify a characteristic of the continuously playing song in accordance with the comparison; and an audio device configured to play the modified portion of the song, during continuous play of the song, to provide auditory guidance.

2. The system of claim 1, wherein the mapping database is configured to map instruments from the user selected song to the obtained parameter information for at least one parameter associated with the medical procedure.

3. The system of claim 2, wherein the audio guidance signal unit is configured to modify an audible characteristic of the instruments from the user selected song in accordance with the comparison.

4. The system of claim 1, wherein the mapping database is configured to map sounds from the user selected song to the obtained parameter information for at least one parameter associated with the medical procedure.

5. The system of claim 4, wherein the audio guidance signal unit is configured to modify an audible characteristic of the sounds from the user selected song in accordance with the comparison.

6. The system of claim 1, wherein the mapping database is configured to store baseline parameter information and the predetermined thresholds for each parameter.

7. The system of claim 1, wherein the mapping database is configured to map the continuously playing user selected song to at least a portion of the medical procedure.

8. The system of claim 1, wherein the obtained parameter information for at least one parameter is a depth and width of an ablation target and the predetermined threshold is a dimensional variance of the depth and the width of the ablation target.

* * * * *

UNITED STATES PATENT AND TRADEMARK OFFICE
CERTIFICATE OF CORRECTION

PATENT NO. : 10,881,376 B2
APPLICATION NO. : 15/807124
DATED : January 5, 2021
INVENTOR(S) : Toam Shemesh et al.

It is certified that error appears in the above-identified patent and that said Letters Patent is hereby corrected as shown below:

On the Title Page
In Item (72), under "Inventors", in Column 1, Line 1, delete "Hertziliya (IL);" and insert -- Herzliya (IL); --, therefor.

In the Specification
In Column 4, Lines 59-60, delete "can be use" and insert -- can be used --, therefor.

Signed and Sealed this
Seventh Day of February, 2023

Katherine Kelly Vidal
Director of the United States Patent and Trademark Office